(12) United States Patent
Dewkar et al.

(10) Patent No.: US 6,872,857 B1
(45) Date of Patent: Mar. 29, 2005

(54) PROCESS FOR CONVERSION OF PHENOL TO HYDROQUINONE AND QUINONES

(75) Inventors: Gajanan Kundali Dewkar, Maharashtra (IN); Vinay Vijayraj Thakur, Maharastra (IN); Sanjeevani Amrit Pardhy, Maharashtra (IN); Arumugam Sudalai, Maharashtra (IN); Sukumar Devotta, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 24 days.

(21) Appl. No.: 10/671,871

(22) Filed: Sep. 29, 2003

(51) Int. Cl.$^7$ .................. C07C 409/00; C07C 37/10; C07C 50/04
(52) U.S. Cl. .................. 568/562; 568/763; 568/771; 552/293
(58) Field of Search .................. 568/562, 763, 568/771; 552/293

(56) References Cited

U.S. PATENT DOCUMENTS

| | | | | |
|---|---|---|---|---|
| 4,317,745 A | * | 3/1982 | Hsieh .................. | 502/159 |
| 4,396,783 A | * | 8/1983 | Esposito et al. ............ | 568/706 |
| 4,442,036 A | * | 4/1984 | Hsu et al. .................. | 552/293 |
| 4,478,752 A | * | 10/1984 | Hsu et al. .................. | 552/293 |
| 4,482,493 A | * | 11/1984 | Matsumoto et al. ........ | 552/310 |
| 5,493,061 A | * | 2/1996 | Ratnasamy et al. ......... | 568/771 |

* cited by examiner

*Primary Examiner*—Johann Richter
*Assistant Examiner*—Sikarl A. Witherspoon

(57) ABSTRACT

The present invention relates to a process for the conversion of phenol to hydroquinone and quinones. More particularly this invention relates to a process for the oxidation of phenol to a mixture of 1,4-benzoquinone and hydroquinone using an oxidant in the presence of titanium superoxide as a reusable catalyst in a liquid phase condition.

13 Claims, No Drawings

PROCESS FOR CONVERSION OF PHENOL TO HYDROQUINONE AND QUINONES

FIELD OF THE INVENTION

The present invention relates to a process for the conversion of phenol to hydroquinone and quinones. More particularly this invention relates to a process for the oxidation of phenol to a mixture of 1,4-benzoquinone and hydroquinone using aq. hydrogen peroxide as the oxidant in the presence of titanium superoxide as a reusable catalyst in a liquid phase condition.

BACKGROUND OF THE INVENTION

Several processes are described in the art for the hydroxylation of phenol to hydroquinone and catechol using hydrogen peroxide as the oxidant and transition metals as catalysts. In the prior art, catalytic conversion of phenol to catechol and hydroquinone has been achieved by the following procedures.

European patent 0266825 (1988), 0265018; U.S. Pat. No. 4,396,783 (1983), 5493061 (1996), UK patent No. 2116974; Japanese patent No. JP 10291948, JP 2001158756, Chinese patent CN 1268502, CN 1129607 all disclose various methods for the use of titanium silicate molecular sieves as catalysts for the hydroxylation of phenol with aq. $H_2O_2$.

Chinese Patent CN 1125642 describes hydroxylation of phenol using Y-zeolite containing transition metals such as Cu, Mn, Fe, Cr, Co with cyclic ligands. Use of metal oxides (including transition, alkali and alkaline earth metals) as catalysts for the oxidation of phenol with $H_2O_2$ in synthesizing benzenediol is reported in Chinese patent No. CN 1134313.

In a continuous process for dihydric phenols using peroxides, Japanese patent JP 55069529 reports 82% conversion of phenol to catechol and hydroquinone with $(CH_3)_2HPO_4$ as catalyst whereas German patent DE 2638559 reports 9% conversion using peracid in the presence of acetylacetone.

European patent [EP $C07CO_{39}$-08, $C07CO_{37}$-60, $C07CO_{37}$-82] claims 55% catechol, 34% hydroquinone by hydroxylation of preheated phenol with propionic acid using ion-exchange resin. A Chinese patent [CN 1167012] reports that the hydroxylation of phenol with aq. $H_2O_2$ has been achieved in low conversion by using nano metal oxide particles and a microporous ion exchanged resin. The reaction of phenol with organic solutions of peroxycarboxylic acids in the presence of chelating agents such as malonic, glutamic, citric or tartaric acid to yield catechol and hydroquinone has been reported in a Brazilian patent German patent DE 2658545 describes phenol hydroxylation using $H_3PO_4$ and $HClO_4$ as catalyst in the presence of benzaldehye to give hydroquinone and catechol. German patent DE 26330302 describes phenol hydroxylation with $H_2O_2$ in $CF_3SO_3H$ containing a small amount of $H_3PO_4$ giving 51% hydroquinone and 23.7% catechol. Slovakian patents [SK 278582 and SK 278569] describe the preparation of benzoquinones by the oxidation of phenols with oxygen in the presence of 2,2' bipyridine-Cu complex in acetonitrile.

Synthesis of 1,4-benzoquinone in 95% yield has been achieved using $MnO_2$ in the presence of aniline. [Zh. Org. Khim. 1990, 26, 2460]. Catalytic oxidation of phenol to p-benzoquinone is reported by using cobalt Schiff base complexes [Fenzi Cuihua 1990, 4, 306 (Chinese)]. The oxidation of phenol in electrochemical reactor with modulated AC voltage produced benzoquinone (43% yield) [J. Appl. Electrochem. 1989, 19, 459].

The abovementioned processes in the prior art are known to be useful for the conversion of phenol to quinones, catechol and hydroquinone. However they suffer from the following drawbacks:

1. Oxidation of phenol with Y-zeolites containing transition metals such as Cu, Mn, Fe, Cr, etc. makes use of expensive cyclic ligands for effective conversion of phenol to hydroquinone; separation of these cyclic ligands is also tedious.
2. $H_3PO_4$, and $HClO_4$, which are corrosive and environmentally hazardous, are used for the oxidation of phenol.
3. Use of sulfonic acid and peroxy carboxylic acids often results in mixture of catechol and hydroquinone with poor selectivity, which makes the separation of products more difficult.
4. Use of benzaldehye adds to the cost of the process and also generates benzoic acid as the side product. This leads to an additional raw material consumption and separation issue.
5. Use of Cu with 2,2-bipyridine or phenanthroline ligands in $CH_3CN$ is a homogeneous process in which catalyst separation from the product is tedious and the catalyst cannot be reused.
6. $MnO2$ is used as the oxidant in presence of aniline; here again the process is homogeneous wherein the separation of product becomes difficult.
7. Co-Schiff base complexes are also used under the homogeneous conditions. The ligands have to be prepared using multi step reaction sequences.
8. In addition to the desired products (quinones and catechol) significant amounts of heavy oxidation products known as tar are also formed in all the processes.

In view of all the above disadvantages of the prior act, it is desirable to provide a process that is safe, inexpensive, heterogeneous and simple to perform.

OBJECTS OF THE INVENTION

The main objective of the present investigation is to provide a new heterogeneous catalytic process for the oxidation of phenol to hydroquinone, which avoids the drawbacks as detailed above.

Another object of the invention is to demonstrate the use of heterogeneous Ti-superoxide (1) as a catalyst for the oxidation of phenol to hydroquinone.

It is another object of the invention to provide a process for the oxidation of phenols, which is environmentally efficient and economical, and avoids the formation of tar by-products.

It is a further object of the invention to provide a simple process for the oxidation of phenol, without affecting the selectivity and activity in the process.

SUMMARY OF THE INVENTION

Accordingly, the present invention provides a heterogeneous catalytic process for the oxidation of phenols which comprises treating a solution of the phenol with an oxidant in the presence of Ti-superoxide (1) heterogeneous catalyst subsequently treating the mixture with water (5 ml) at 100° C. and then terminating the reaction by bringing the reaction mixture to room temperature, extracting the product by conventional methods like solvent extraction and purifying by conventional methods to obtain the oxidized phenol.

In one embodiment of the invention, the strength of the oxidant $H_2O_2$ is in the range of 10–90%, preferably around 30–50%.

In one embodiment of the invention, the oxidant comprises 10–50% of aq. $H_2O_2$.

In another embodiment of the invention, the oxidant comprises 30% of aq. $H_2O_2$.

In another embodiment of the present invention, the phenol solution comprises a solution of phenol in a solvent, which may be selected from a range of organic solvents such as, but are not limited to, acetonitrile, acetone, methanol and acetic acid. Water also can be used as the solvent.

In another embodiment, a variety of phenols (where R=H, Me, Cl, Br, I, t-Bu, etc.) can be converted to the corresponding quinones in excellent yield and selectivity.

In another embodiment of the invention, the phenol is selected from the group consisting of phenol, o-cresol, m-cresol, 2,6-dimethylphenol, 2-butylphenol, 2,6-dibutylphenol, 4-chlorophenol, 4-bromophenol, 4-iodophenol and 2,4-dichlorophenol.

In another embodiment of the invention, the reaction of the phenol with acetic acid and hydrogen peroxide is carried out at a temperature in the range of 50–60° C. and for a time period of 1–10 h.

In another embodiment of the invention, the conversion of the phenol is up to 100% and the selectivity of the catalyst is up to 990/A.

DETAILED DESCRIPTION OF THE INVENTION

The present invention provides a new heterogeneous catalytic process for the oxidation of phenols, which comprises treating a solution of phenol in acetic acid with 30% aq. $H_2O_2$ in the presence of Ti-superoxide (1) heterogeneous catalyst. Ti-superoxide catalyst was synthesized (Scheme 1) in the laboratory and successfully used for oxidation of amines to nitro compounds [Angew. Chem. Int. Ed. Engl. 2001, 40, 405–408]

Scheme 1: (i) MeOH, 25° C., 2 h.

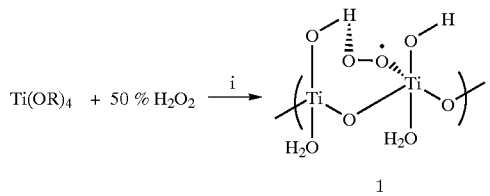

R = $^i$Pr, $^n$Bu
n being in the range of 1–20

The temperature is preferably in the range of 50–60° C. and the reaction is preferably carried out for a time period in the range of 1–10 h. After this step, the reaction mixture is treated with water (5 ml) at 100° C. and then the reaction terminated by bringing the reaction mixture to room temperature. The product can be extracted by any conventional method such as like solvent extraction and the product is then purified by any conventional method to obtain the product (Scheme 2).

Scheme 2: (i) cat. Ti-superoxide (1), 30 % $H_2O_2$, AcOH, 50–60° C.;
(ii) water, reflux (100° C.)

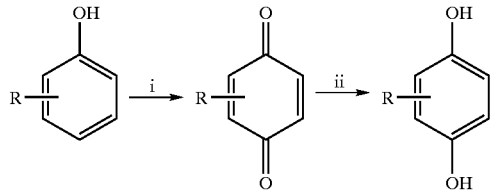

R = H, alkyl, halide, etc.

The strength of the oxidant i.e. $H_2O_2$ can be in the range 10–90%, and most preferably around 30–50%. The solvent used can be selected from a range of organic solvents such as, but are not limited to, acetonitrile, acetone, methanol and acetic acid. Water also can be used as the solvent.

A large range of phenols where R=H, Me, Cl, Br, 1, 1-Bu, etc. can be converted to the corresponding quinones in excellent yield and selectivity.

The present invention provides a new heterogeneous catalytic process for the oxidation of phenol to hydroquinone, which avoids the drawbacks as detailed above. More particularly the present invention demonstrates the use of heterogeneous Ti-superoxide (1) as a catalyst for the oxidation of phenol to hydroquinone. Ti-superoxide catalyst was synthesized (Scheme 1) in our laboratory and successfully used for oxidation of amplifies to nitro compounds [Angew. Chem. Int. Ed. Engl. 2001, 40, 405–408]

Scheme 1: (i) MeOH, 25° C., 2 h.

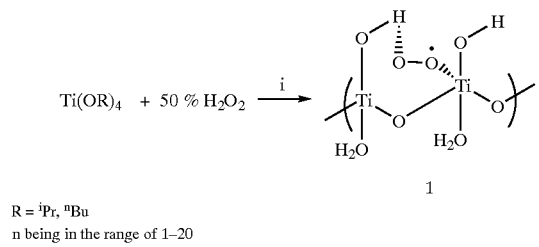

R = $^i$Pr, $^n$Bu

Preparation of Ti-superoxide catalyst: aq. 50% $H_2O_2$ (5.98 g, 0.175 mol) is added slowly to a solution of Ti(OPr)$_4$ (5.0 g, 0.0175 mol) in anhydrous MeOH (50 ml) over 40 minutes under $N_2$ with stirring at room temperature. The yellow precipitate that formed is collected by filtration on a sintered funnel, washed with anhydrous methanol and dried under reduced pressure (3 mm Hg) at 25° C. for 1 h to afford 3.94 g (98%) of Ti-superoxide (1) catalyst.

The process of the present invention is described herein with reference to examples, which are illustrative only and should not be construed to limit the scope of the present invention in any manner.

EXAMPLE 1

Preparation of 1,4-hydroquinone

A mixture of phenol (5 mmol) and Ti-superoxide catalyst (125 mg, 20% w/w) in acetic acid (5 ml) was heated with stirring at 50–60° C. under inert atmosphere. To this' reaction mixture was added aq. 10% $H_2O_2$ (20 mmol) drop wise over 15 min. and heated for 2 h. After this, water (5 ml) was added and the reaction mixture was heated to reflux for 8 h. The catalyst was recovered by simple filtration and 1,4-hydroquinone formed (20%) was separated by chromatographic purification.

EXAMPLE 2

Preparation of 1,4-hydroquinone

A mixture of phenol (5 mmol) and Ti-superoxide catalyst (125 mg, 20% w/w) in acetic acid (5 ml) was heated with stirring at 50–60° C. under inert atmosphere. To this reaction mixture was added aq. 50% $H_2O_2$ (20 mmol) drop wise over 15 min. and heated for 1 h. After this, water (5 ml) was added and the reaction mixture was heated to reflux for 7 h. The catalyst was recovered by simple filtration and 1,4-hydroquinone formed (61%) was separated by chromatographic purification.

EXAMPLE 3

Preparation of 1,4-hydroquinone

A mixture of phenol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2O_2$ (20 mmol) drop wise over 15 min. and heated for 1 h. After this, water (5 ml) was added and the reaction mixture was heated to reflux for 6 h. The catalyst was recovered by simple filtration and 1,4-hydroquinone formed (60%) was separated by chromatographic purification.

EXAMPLE 4

Preparation of 1,4-hydroquinone

A mixture of phenol (5 mmol) and Ti-superoxide catalyst (250 mg, 40% w/w) in acetic acid (5 ml) was heated with stirring at 50–60° C. under inert atmosphere. To this reaction mixture was added aq. 30% $H_2O_2$ (20 mmol) drop wise over 15 min. and heated for 1 h. After this, water (5 ml) was added and the reaction mixture was heated to reflux for 6 h. The catalyst was recovered by simple filtration and 1,4-hydroquinone formed (63%) was separated by chromatographic purification.

EXAMPLE 5

Preparation of 1,4-benzoquinone

A mixture of phenol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2O_2$ (20 mmol) drop wise over 15 min. and heated for 1 h. The catalyst was recovered by simple filtration and 1,4-benzoquinone formed (88%) was separated by chromatographic purification.

EXAMPLE 6

Preparation of 2-methyl-1,4-benzoquinone

A mixture of o-cresol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2O_2$ (20 mmol) drop wise over 15 min. and heated for 1 h. The catalyst was recovered by simple filtration and 2-methyl-1,4-benzoquinone formed (96%) was separated by chromatographic purification.

EXAMPLE 7

Preparation of 2-methyl-1,4-benzoquinone

A mixture of m-cresol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2O_2$ (20 mmol) drop wise over 15 min. and heated for 1 h. The catalyst was recovered by simple filtration and 2-methyl-1,4-benzoquinone formed (99%) was separated by chromatographic purification.

EXAMPLE 8

Preparation of 2,6-dimethyl-1,4-benzoquinone

A mixture of 2,6-dimethylphenol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2O_2$ (20 mmol) drop wise over 15 min. and heated for 1 h. The catalyst was recovered by simple filtration and 2,6-dimethyl-1,4-benzoquinone formed (97%) was separated by chromatographic purification.

EXAMPLE 9

Preparation of 2-tert-butyl-1,4-benzoquinone

A mixture of 2-1-butylphenol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2O_2$ (20 mmol) drop wise over 15 min. and heated for 1 h. The catalyst was recovered by simple filtration and 2-tert-butyl-1,4-benzoquinone formed (97%) was separated by chromatographic purification.

EXAMPLE 10

Preparation of 2,6-di-tert-butyl-1,4-benzoquinone

A mixture of 2,6-di-t-butylphenol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2O_2$ (20 mmol) drop wise over 15 min. and heated for 3 h. The catalyst was recovered by simple filtration and 2,6-di-tert-butyl-1,4-benzoquinone formed (65%) was separated by chromatographic purification.

EXAMPLE 11

Preparation of 1,4-benzoquinone

A mixture of 4-chlorophenol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2O_2$ (20 mmol) drop wise over 15 min. and heated for 1 h. The catalyst was recovered by simple filtration and 1,4-benzoquinone formed (55%) was separated by chromatographic purification.

EXAMPLE 12

Preparation of 1,4-benzoquinone

A mixture of 4-bromophenol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2 1\%$ (20 mmol) drop wise over 15 min. and heated for 1 h. The catalyst was recovered by simple filtration and 1,4-benzoquinone formed (60%) was separated by chromatographic purification.

EXAMPLE 13

Preparation of 1,4-benzoquinone

A mixture of 4-iodophenol (5 mmol) and Ti-superoxide catalyst (125 mg, 20% w/w) in acetic acid (5 ml) was heated with stirring at 50–60° C. under inert atmosphere. To this reaction mixture was added aq. 30% $H_2O_2$ (20 mmol) drop wise over 15 min. and heated for 1 h. The catalyst was recovered by simple filtration and 1,4-benzoquinone formed (75%) was separated by chromatographic purification.

EXAMPLE 14

Preparation of 2-chloro-1,4-benzoquinone

A mixture of 2,4-dichlorophenol (5 mmol) and Ti-superoxide catalyst (125 mg, 20% w/w) in acetic acid (5 ml) was heated with stirring at 60–70° C. under inert atmosphere. To this reaction mixture was added aq. 30% $H_2O_2$ (20 mmol) drop wise over 15 min. and heated for 1 h. The catalyst was recovered by simple filtration and corresponding quinone formed (25%) was separated by chromatographic purification.

TABLE 1

Ti-superoxide (1) catalyzed oxidation of phenols to quinines and hydroquinones with aq. 30% $H_2O_2$:[a]

| Ex. No. | Substrate | t/h | Conversion (%) | Product[b] Quinone | HQ[d] | Selectivity (%)[c] |
|---|---|---|---|---|---|---|
| 1. | Phenol | 10 | 22 | 2 | 20[e] | 91.0 |
| 2. | Phenol | 8 | 66 | 5 | 61[f] | 92.4 |
| 3. | Phenol | 7 | 65 | 3 | 60 | 92.3 |
| 4. | Phenol | 7 | 68 | 3.5 | 63[g] | 92.7 |
| 5. | Phenol | 1 | 92 | 88 | 2.3 | 95.7 |
| 6. | o-Cresol | 1 | 99 | 96 | 3.0 | 97.0 |
| 7. | m-Cresol | 1 | 100 | 99 | 0.5 | 99.0 |
| 8. | 2,6-Dimethylphenol | 1 | 100 | 97 | 2.0 | 97.0 |
| 9. | 2-[t]Butylphenol | 1 | 99 | 97 | 0.7 | 98.0 |
| 10. | 2,6-Di[t]butylphenol | 3 | 70 | 65 | 2.0 | 93.0 |
| 11. | 4-Chlorophenol | 1 | 57 | 55 | — | 96.5 |
| 12. | 4-Bromophenol | 1 | 61 | 60 | — | 98.4 |
| 13. | 4-Iodophenol | 1 | 77 | 75 | — | 97.4 |
| 14. | 2,4-Dichlorophenol | 1 | 32 | 25 | 5.0 | 78.1 |

[a]See examples for detailed experimental procedure; [b]determined by GC analysis of the crude product; [c]selectivity to hydroquinone; [d]hydroquinone; [e]aq. 10% $H_2O_2$; [f]aq. 50% $H_2O_2$; [g]40% w/w catalyst.

The advantages of the present invention are:
1. The unique advantage of the present process is that the quinone formed initially after the oxidation of phenol can be converted to hydroquinone by heating with water at 100° C.
2. Yet another advantage of this process is that the catalyst can be recovered and reused for several times without affecting the catalytic activity and the selectivity of the process.
3. The process is economically viable
4. It is environmentally safe
5. It is easy to handle
6. It is time saving
7. No tar formation is observed in contrast to the existing processes.

We claim:
1. A process for the oxidation of phenols which comprises treating a solution of the phenol with an oxidant in the presence of Ti-superoxide heterogeneous catalyst of formula 1,

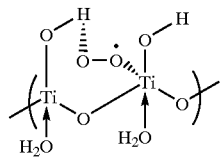

n being in the range of 1–20, followed by subsequently treating the mixture of phenol solution and oxidant and catalyst with water at a temperature of about 100° C., and then terminating the reaction by bringing the reaction mixture to room temperature, extracting and purifying the product to obtain the oxidized phenol.

2. A process as claimed in claim 1 wherein the strength of the oxidant $H_2O_2$ is in the range of 10–90%, preferably around 30–50%.

3. A process as claimed in claim 1 wherein the oxidant comprises 10–50% of aq. $H_2O_2$.

4. A process as claimed in claim 1 wherein the oxidant comprises 30% of aq. $H_2O_2$.

5. A process as claimed in claim 1 wherein the phenol solution comprises a solution of phenol in a solvent selected from an organic solvent or water.

6. A process as claimed in claim 5 wherein the organic solvent is selected from the group consisting of acetonitrile, acetone, methanol and acetic acid.

7. A process as claimed in claim 1 wherein the phenol is a substituted phenol.

8. A process as claimed in claim 7 wherein the substituent on the phenol is selected from the group consisting of H, Me, Cl, Br, I and t-Bu.

9. A process as claimed in claim 1 wherein the phenol is selected from the group consisting of phenol, o-cresol, m-cresol, 2,6-dimethylphenol, 2-butylphenol, 2,6-dibutylphenol, 4-chlorophenol, 4-bromophenol, 4-iodophenol and 2,4-dichlorophenol.

10. A process as claimed in claim 1 wherein the reaction of the phenol in solution with the oxidant is carried out at a temperature in the range of 50–80° C. and for a time of 1–10 h.

11. A process as claimed in claim 10 wherein the temperature is in the range of 50–60° C. and the time period is in the range of 1 to 3 hours.

12. A process as claimed in claim 1 wherein the phenol is converted at up to 100% and the catalyst shows a selectivity of up to 99%.

13. A process as claimed in claim 1 wherein the catalyst is recycled to the reactor.

* * * * *